United States Patent
Stopp et al.

(10) Patent No.: US 12,263,031 B2
(45) Date of Patent: Apr. 1, 2025

(54) DETERMINING A CONFIGURATION OF A MEDICAL X-RAY IMAGING SYSTEM FOR DETECTING A MARKER DEVICE

(71) Applicant: Brainlab AG, Munich (DE)

(72) Inventors: Sebastian Stopp, Munich (DE); Nils Frielinghaus, Munich (DE)

(73) Assignee: Brainlab AG, Munich (DE)

( * ) Notice: Subject to any disclaimer, the term of this patent is extended or adjusted under 35 U.S.C. 154(b) by 224 days.

(21) Appl. No.: 18/009,941

(22) PCT Filed: Jul. 6, 2020

(86) PCT No.: PCT/EP2020/069027
§ 371 (c)(1),
(2) Date: Dec. 12, 2022

(87) PCT Pub. No.: WO2022/008035
PCT Pub. Date: Jan. 13, 2022

(65) Prior Publication Data
US 2023/0263500 A1    Aug. 24, 2023

(51) Int. Cl.
| | |
|---|---|
| A61B 6/00 | (2024.01) |
| A61B 6/06 | (2006.01) |
| A61B 6/58 | (2024.01) |
| A61B 90/00 | (2016.01) |
| G06T 7/33 | (2017.01) |
| G06T 7/73 | (2017.01) |

(52) U.S. Cl.
CPC ............... *A61B 6/587* (2013.01); *A61B 6/06* (2013.01); *A61B 6/4435* (2013.01); *A61B 90/39* (2016.02); *G06T 7/337* (2017.01); *G06T 7/74* (2017.01); *A61B 2090/3966* (2016.02)

(58) Field of Classification Search
None
See application file for complete search history.

(56) References Cited

U.S. PATENT DOCUMENTS

2020/0121267 A1    4/2020    Deutschmann

FOREIGN PATENT DOCUMENTS

| EP | 3273861 A1 | | 1/2018 |
|---|---|---|---|
| WO | WO2013127005 | * | 6/2013 |
| WO | 2013127005 A1 | | 9/2013 |
| WO | 2016156150 A1 | | 10/2016 |

OTHER PUBLICATIONS

Written Opinion of the International Searching Authority dated Mar. 9, 2021 for Application Serial No. PCT/EP2020/069027, 6 Pages.
International Search Report dated Mar. 9, 2021 for Application Serial No. PCT/EP2020/069027, 3 Pages.

* cited by examiner

*Primary Examiner* — Hoon K Song
(74) *Attorney, Agent, or Firm* — Tucker Ellis LLP (57) ABSTRACT

This document relates to technologies of determining a configuration of a medical imaging system comprising an x-ray source and an x-ray detector mounted on a gantry and an x-ray source collimator for shaping the x-ray beam emitted by the x-ray source, wherein at least one of the x-ray source and the x-ray detector is movable along the gantry. The configuration of the medical imaging system comprises the position of the x-ray source, the position of the x-ray detector and the settings of the x-ray source collimator and is to be used for capturing a marker image, wherein the position of the marker device can be calculated using the marker image.

13 Claims, 5 Drawing Sheets

DETERMINING A CONFIGURATION OF A MEDICAL X-RAY IMAGING SYSTEM FOR DETECTING A MARKER DEVICE

RELATED APPLICATION DATA

This application is a National Phase application of International Application No. PCT/EP2020/069027, filed Jul. 6, 2020, the contents of which are incorporated herein by reference.

FIELD OF THE INVENTION

The present invention relates to a method of determining a configuration of a medical x-ray imaging system to be used for capturing a marker image showing a marker device, a method of determining the position of the marker device, a computer program, a computer, a system and a non-transitory computer-readable storage medium.

TECHNICAL BACKGROUND

Medical imaging systems for obtaining fluoroscopic or x-ray images are typically used for planning surgeries, for verification of information immediately before surgery or for imaging a patient during surgery.

It is also known to track the position of objects, such as medical instruments, using optical, magnetic or electromagnetic tracking. A marker device, which typically comprises a plurality of markers, is attached to the object in a known or measured spatial relationship and a tracking system is used to measure the position of the marker device. The markers are typically optical or electromagnetic markers which can be detected using a (stereoscopic) camera or an electromagnetic detector. The present invention now uses markers which are detectable in an x-ray image, the marker image, such that the medical imaging system can be used for detecting the marker device and an additional, dedicated tracking system is not necessary.

The medical imaging system comprises an x-ray source and an x-ray detector mounted on a gantry and an x-ray source collimator for shaping the x-ray beam emitted by the x-ray source, thus generating a shaped x-ray beam. At least one of the x-ray source and the x-ray detector is movable along the gantry. The gantry is a carrier which carries the x-ray source, the x-ray detector and the collimator. Typical embodiments are a C-arm or a ring-shaped carrier. At least one of the x-ray source and the x-ray detector are movable along the gantry, such that the medical imaging system does not have a fixed isocenter. This means that the field-of-view of the medical imaging system is adjustable by moving the x-ray source and/or the x-ray detector and shaping the x-ray beam using the collimator. The invention is in particular usable in connection with the Loop-X® medical imaging system which is a product of Brainlab AG and in which an x-ray source and an x-ray detector are mounted on a circular gantry and are independently movable along the gantry.

The present invention has the object of finding a configuration of the medical imaging system such that the marker device is detectable and the radiation exposure on the patient is acceptable.

The present invention can be used for procedures e.g. in connection with a medical imaging system such as Loop-X® of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

This document relates to technologies of determining a configuration of a medical imaging system comprising an x-ray source and an x-ray detector mounted on a gantry and an x-ray source collimator for shaping the x-ray beam emitted by the x-ray source, wherein at least one of the x-ray source and the x-ray detector is movable along the gantry. The configuration of the medical imaging system comprises the position of the x-ray source, the position of the x-ray detector and the settings of the x-ray source collimator.

The positions of the x-ray source and the x-ray detector can be reached by moving both the x-ray source and the x-ray detector along the gantry or by moving the gantry, in particular by rotating it in the plane in which the gantry lies, and moving one of the x-ray source or the x-ray detector relative to the gantry.

GENERAL DESCRIPTION OF THE INVENTION

In this section, a description of the general features of the present invention is given for example by referring to possible embodiments of the invention.

In general, the invention reaches the aforementioned object by providing, in a first aspect, a method of determining a configuration of a medical imaging system as briefly described above. The configuration comprises the position of the x-ray source, the position of the x-ray detector and the settings of the x-ray source collimator. The medical imaging system is to be used for capturing a marker image showing a marker device. The marker device for example comprises one or more markers in a known geometrical arrangement. The markers are for example radiopaque.

In this document, determining means for example deriving, deducting or calculating, but not a detection of a current status. So for example the configuration of the medical imaging system is a theoretical target position rather than the actual configuration.

The method comprises a step of acquiring patient position data representing the position of a patient relative to the medical imaging system. In one example, the patient position data describes the position of a patient reference system assigned to the patient in an imaging system reference system assigned to the medical imaging system. In this document, a position or a relative position is given in up to 3 translational dimensions and/or up to 3 rotational dimensions.

The method further comprises the step of acquiring approximate marker position data representing the approximate position of the marker device relative to the medical imaging system. In one example, the approximate marker position data is given in the imaging system reference system. The marker position data for example describes a particular three-dimensional volume in which the marker device is expected to be located or a position of a generic model of the marker device, for example as the position of a reference of this model in the imaging system reference system.

The method further comprises the step of calculating the configuration of the medical imaging system from the patient position data, the approximate marker position data and based on a trade-off between the radiation exposure on the patient when capturing the marker image and a second criteria being at least one of the visibility of the marker device in the marker image and the expected imaging quality of the marker device in the marker image.

By using the medical imaging system for detecting the marker device, it is not necessary to use a dedicated tracking system. On the other hand, capturing an x-ray image has the risk of exposing the patient with radiation. It is therefore a goal to limit this radiation exposure, for example as much as possible, while ensuring that the position of the marker device can be detected as accurately as required.

The radiation exposure can be represented by a radiation exposure metric. This radiation exposure metric for example linearly correlates to the radiation dose applied to the patient when capturing a marker image.

In one embodiment, the visibility of the marker device in the marker image represents at least one of the portion of the marker device which lies within the shaped x-ray beam and the orientation of the marker device relative to the x-ray source. The visibility is for example represented by a visibility metric.

In the first aspect, the visibility of the marker device means how much of the marker device is visible in the marker image. In one example, the visibility of the marker device, and thus the visibility metric, can be the number of markers of the marker device which are visible in the marker image compared to the total number of markers of the marker device. In another example, the visibility of the marker device classifies the markers of the marker device into categories such as completely visible, partly visible and not visible in the marker image and calculates the visibility metric based on this classification. For example, a completely visible marker is assigned the value 1, a partly visible marker is assigned the value 0.5 and a non-visible marker is assigned the value 0 and the metric is the sum of the values assigned to all markers of the marker device.

In the second aspect, the orientation of the marker device influences the visibility of the marker device because one or more markers of the marker device can occlude one or more other markers of the marker device in the marker image. The metric can for example be the number of unoccluded markers of the marker device in the marker image.

In this document, the expected imaging quality of the marker device in the marker image represents how clearly the marker device can be seen in the marker image and is for example represented by an imaging quality metric. The imaging quality can for example depend on the area of the marker image in which the marker device is depicted. Depending on the components of the medical imaging system, imaging quality, such as sharpness and/or contrast, can decrease towards the borders of the marker image. This means that the imaging quality metric might represent the distance of the marker device in the marker image from the center of the marker image. An alternative or additional aspect of the expected imaging quality can be the angle between the center of the x-ray beam emitted by the x-ray source and the surface of the x-ray detector. The best imaging quality is achieved if the x-ray beam is orthogonal to the surface of the x-ray detector. If this angle decreases, distortions occur which decrease the expected imaging quality. The imaging quality metric can thus be the offset between the angle at which the x-ray beam hits the surface of the x-ray detector from 90°. The imaging quality metric can be calculated based on one or more of the aspects described above.

A collimator for shaping an x-ray beam typically comprises one or more movable parts which are adjustable for blocking and/or guiding the x-ray radiation. The settings of the x-ray source collimator for example describe the positions of the movable parts of the collimator.

The trade-off for example involves or is a metric calculated from the radiation exposure and the second criterion. This metric is for example calculated by weighting the radiation exposure metric and the metric of the second criterion. The weights applied typically depend on the particular constellation defined, for example, by a patient, the surgery to be performed or other parameters.

In one embodiment, the trade-off includes calculating a metric from the radiation exposure metric and the metric of the second criterion and calculating the configuration of the medical imaging system involves optimizing the metric. As discussed above, the metric can be a weighted combination of metrics, such as the radiation exposure metric and a metric of the second criterion, but also other metrics described herein. Optimizing can mean minimizing or maximizing the metric but is no limited thereto. It could also mean finding an acceptable configuration, which can mean that the metric is below or above a threshold.

In one embodiment, the trade-off further represents the size of the shaped x-ray beam. The size preferably means the size of the cross-section of the shaped x-ray beam. It usually advantageous to have a shaped x-ray beam being as small as possible to minimize the radiation exposure on the patient, for example by scattering of the x-ray radiation. The size of the shaped x-ray beam can have an associated beam size metric, for example the opening angle of the shaped x-ray beam or the size of the cross-section of the shaped x-ray beam at a defined distance to the x-ray source collimator. The size can be calculated from the setting of the x-ray source collimator.

In one embodiment, if a plurality of two or more marker images is to be captured, the trade-off further represents the viewing directions between the shaped x-ray beams emitted when the plurality of marker images are captured. In order to determine the location of the marker device, it is advantageous if this determination can be based on a plurality of marker images which are captured from non-parallel viewing directions. It is ideal if the viewing directions are orthogonal to each other, or at least almost orthogonal. In an exemplary implementation, the metric of the trade-off further includes a viewing direction metric which quantifies the difference between the viewing directions. In one example, the viewing direction metric is the deviation of the difference between two viewing directions from 90 degrees. This deviation can be weighted to be included in the metric of the trade-off.

In this document, the viewing direction of a marker image is used synonymously with the viewing direction of the shaped x-ray beam as generated by the x-ray source in combination with the x-ray source collimator. The viewing direction of the shaped x-ray beam can be the central axis of the shaped x-ray beam. The shaped x-ray beam is for example a cone beam, wherein the central axis of this cone corresponds to the viewing direction of the shaped x-ray beam.

In one exemplary embodiment, the approximate marker position data is acquired based on at least one of an x-ray image of the patient which also shows at least part of the marker device, position data obtained from a medical tracking system, planning data describing a procedure to be performed using the medical imaging system, optical image data obtained by an optical camera of the medical imaging system and robot position data representing the position of a robot carrying the marker device.

An x-ray image of the patient which also shows at least part of the marker device can be an x-ray image which is captured using the medical imaging system anyway for other purposes, such as analyzing the current status of the patient. If this x-ray image shows at least a part of the marker device, the position of the marker device can be approximated based on the position of the x-ray source and the position of the x-ray detector when the x-ray image was captured and the position of the marker device in the x-ray image.

Position data obtained from a medical tracking system means that the marker device, or another marker device associated with the marker device, is tracked by a medical tracking system which is not the medical imaging system. The medical tracking system can for example be an optical, magnetic or electromagnetic tracking system. This medical tracking system can either track the marker device itself or a dedicated marker device having a known spatial relationship to the marker device.

Some medical imaging systems comprise an optical camera. In this case, an optical image obtained by this optical camera can be analyzed to identify the marker device and its approximate position relative to the medical imaging system. It is for example possible to identify the centers of the markers in the optical image, to calculate line in space, in the imaging system reference system, on which the centers lie, and to match the known geometry of the marker device with those lines in space.

In some scenarios, a robot is used in combination with the medical imaging system. The robot typically carries a medical instrument at its free end. The marker device is in a known spatial relationship to the medical instrument, such that the position of the medical instrument can be derived from the position of the marker device and vice versa. If the robot carries the marker device, then the position of the marker device can be approximated from the status of the robot, such as the positions of the joints of the robot, and the position of the medical instrument at the free end. This information can be obtained for example by measuring the joint positions or using target joint positions calculated by a computer for moving the robot, and in particular the medical instrument, into a desired position. Starting from the position of the base of the robot, the position of the medical instrument can be calculated by applying the joint positions to a kinematic model of the robot.

In one exemplary embodiment, the patient position data is determined based on at least one of a 3D scan of the patient, sampling a plurality of points on the surface of the patient and performing 2D/3D registration of 3D image data of the patient with one or multiple two-dimensional images of the patient.

A 3D scan of the patient can be performed using known procedures, such as ones using a 3D scanner like a laser scanner, a structured light 3D scanner, a time-of-flight camera, a CT scanner or an MRI scanner. This results in a 3D scan relative to the 3D scanner. With the information regarding the relative position between the 3D scanner and the medical imaging system, the position of the patient relative to the medical imaging system can be calculated.

Sampling a plurality of points on the surface of the patient is for example performed using a tracked pointer. Such a pointer has a tip which is held against the surface of the patient and a pointer marker device attached to the pointer is tracked in order to determine the position of the tip of the pointer and thus the location of the point on the surface of the patient.

Performing 2D/3D registration of 3D image data of the patient with one or multiple two-dimensional images of the patient uses existing 3D image data, for example captured in a planning phase using a 3D imaging system such as a CT or MRT imaging device or an optical 3D camera. The 3D image data represents a 3D model of the patient. One or multiple two-dimensional images of the patient can then be used to find an orientation of the 3D image data in space such that the one or multiple two-dimensional images of the patient would result. This is a known technique, for example using digitally reconstructed radiographs (DRRs) for two-dimensional x-ray images of the patient or matching the shape of the contour of the patient with the shape extracted from optical two-dimensional images of the patient. It is also possible to find feature points in an optical two-dimensional image, such as landmarks, and to match the 3D image data onto the feature points.

In one exemplary embodiment, the radiation exposure on the patient is calculated as the overall x-ray dose applied to the patient or as the sum of the x-ray dose applied to different regions of the patient multiplied by weight factors corresponding to said different regions. The latter approach takes into account different vulnerabilities of different regions of the patient regarding x-ray radiation. The different regions of the patient may have assigned corresponding vulnerabilities, for example using an atlas of the patient or being indicated in a surgical plan or a pre-operative scan of the patient. The higher the vulnerability of a particular region, the higher the weight factor for said region.

In one exemplary embodiment, the configuration of the medical imaging system is determined in two steps. The first step involves calculating a preliminary configuration of the medical imaging system, capturing a preliminary marker image by the medical imaging system using the preliminary configuration and calculating the approximate marker position data from the preliminary marker image. The preliminary configuration can for example comprise collimator settings resulting in a rather narrow x-ray beam and/or positions of the x-ray source and/or the x-ray detector such that the shaped x-ray beam does not propagate through the patient. This might, however, lead to a marker image which does not show all of the marker device.

The second step involves calculating the configuration of the medical imaging system based on the approximate marker position data. With the information regarding the approximate marker position data determined in the first step, a proper configuration of the medical imaging system can be calculated, for example by broadening the shaped x-ray beam such that more of the marker device is visible in the marker image or by re-positioning the x-ray source and/or the x-ray detector such that the marker device is depicted in a more central region of the marker image.

In one exemplary embodiment, if the medical imaging system is to be used for determining the position of multiple marker devices, the configuration of the medical imaging system is calculated from the patient position data, the approximate marker position data of all of the multiple marker devices and based on a trade-of between the radiation exposure on the patient when capturing the marker image and a second criterion being at least one of the visibility of at least one of the multiple marker devices in the marker image and the expected imaging quality of at least one of the multiple marker devices in the marker image. In particular, the second criterion covers each of the multiple marker devices. If there are for example two marker devices, the second criterion can be the visibility of one marker device and the expected image quality of the other marker, the visibility of both marker devices, the visibility of both marker devices and the expected image quality of one of the marker devices, the expected image quality of both marker devices or the visibility of one of the marker devices and the expected image quality of both marker devices. For more than two marker devices, any permutation can be used.

The metric of the second criterion is based on the visibility of at least one of the marker devices and the expected imaging quality of at least one of the marker devices depending on the particular application. For example, weights or the different visibilities for the different expected image qualities can be applied when calculating the metric as desired.

In one implementation of this embodiment, the method determines a plurality of configurations of the medical imaging system for capturing a plurality of marker images. In one example, a first configuration is calculated which leads to a first marker image in which at least two out of the multiple marker devices are completely or at least partly shown. A second configuration leads to a second marker image in which one of the multiple marker devices is shown and a third configuration leads to a third marker image in which another one of the multiple marker devices is shown. The viewing direction of the first marker image advantageously perpendicular to the viewing directions of the second marker image and the third marker image, respectively, or at least within a certain range, such as 60°-90°, 70°-90°, 80°-90° or 85°-90°.

The two marker devices can have different accuracy requirements or characteristics which could be taken into account when calculating the configuration or the configurations of the medical imaging system. This relates in particular to the visibility of a marker device in the marker image and a desired imaging quality of the marker device in the marker image.

In another embodiment, the method calculates two or more configurations of the medical imaging system. The first configuration is one in which the radiation exposure on the patient compared to the second criterion is weighted stronger than for the second configuration. A first marker image captured using the first configuration is then used to determine or modify the approximate marker position data which is then used for calculating the second configuration of the medical imaging system.

In general, the method can calculate two or more configurations of the medical imaging system, for example for having different viewing directions onto the marker device. The two or more configurations can be optimized jointly, for example by optimizing an overall metric calculated from the metrics of the two or more configurations. Weights can be assigned to the metrics of the respective configurations, for example for prioritizing one or more viewing directions.

In one exemplary embodiment of the invention, calculating the configuration of the medical imaging system involves acquiring an initial configuration and modifying the initial configuration based on the patient position data. The initial configuration is a template considering the radiation exposure on the patient and the second criterion. The initial configuration is then only adapted to the actual position of the patient. As an option, the initial configuration is further modified to obtain the configuration considering the size of the patient.

Taking a standard deep brain stimulation procedure on the head of the patient as an example, there is a standardized initial configuration of the medical imaging system that only needs to be slightly optimized for differences in the patient position, in particular the position of the head relative to the medical imaging system, and the anatomy of the patient, in particular the size of the head. The size of the head can for example be derived from pre-operative imaging. It is also possible to have an operator align the head of the patient to the center of the medical imaging system with the help of for example laser indicators.

In one embodiment, calculating the configuration of the medical imaging system involves a numerical optimization process which has the patient position data and the approximate marker position data as input parameters. The output parameters are the position of the x-ray source, the position of the x-ray detector and the settings of the x-ray source collimator. The numerical optimization process calculates the radiation exposure on the patient and the second criterion, that is at least one of the visibility of the marker device in the marker image and the expected imaging quality of the marker device in the marker image, for a particular hypothetical configuration. The numerical optimization process optimizes the configuration of the medical imaging system using particular weights for the radiation exposure and the second criterion. The numerical optimization process might calculate a marker device tracking accuracy from the second criterion, for example by simulating the effect of misdetection due to varying detector resolution and/or sensitivity over the detector surface. When optimizing the configuration, exemplary weights could be that 0.1 mm gain in the tracking resolution weighs as much as 0.1 mSv radiation dose normal tissue of the patient. However, as explained above, the weight of the radiation exposure might depend on the type of tissue of the patient subject to the radiation.

The numerical optimization process calculates a metric for each tested hypothetical configuration of the medical imaging system and optimizes this metric using known mathematical approaches, resulting in a final configuration of the medical imaging system which is then output.

In one exemplary implementation, the x-ray source and the x-ray detector are movable in a reference plane of the medical imaging system. The approximate position of the marker device and the center of the patient's head are projected into the reference plane. A line is drawn within the reference plane form the center of the head to the approximate position of the marker device. A first viewing direction of the shaped x-ray beam is set to be at an offset angle to the drawn line in a first direction. The positions of the x-ray source and the x-ray detector are for example set such that the detector surface of the x-ray detector is parallel to the first viewing direction and the center of the unshaped x-ray beam emitted by the x-ray source is parallel to the first viewing direction. The settings of the x-ray source collimator are then determined such that the marker device lies within the shaped x-ray beam and the radiation exposure on the patient is minimized.

Then a second configuration can be calculated in which the viewing direction is rotated by an offset angle from the drawn line in a second direction opposite to the first direction. The positions of the x-ray source and the x-ray detector as well as the settings of the x-ray source collimator are then determined in analogy to the first configuration. The two offset angles may be the same, like 45°, or different, for example in a range from 40° to 50°.

Then the radiation exposure on the patient is calculated, based on the first and second configurations. It is then determined whether or not the radiation exposure is acceptable, for example by comparing it to a threshold. In one implementation, the radiation exposure on the patient might not be acceptable. In this case, the angles for the viewing directions can be increased from the respective offset angle to a larger angle, such as 50°, 55° or 60° and the process is repeated for those two viewing directions. Increasing the angles of the viewing directions can be made iteratively until the radiation exposure on the patient is acceptable.

The present invention also relates, in a second aspect, to a method determining the position of a marker device relative to a medical imaging system comprising an x-ray source and an x-ray detector mounted on a gantry and an x-ray source collimator for shaping the beam of the x-ray source, wherein at least one of the x-ray source and the x-ray detector is movable along the gantry as explained above. The method includes determining the configuration of the medical imaging system according to the method described above, capturing a marker image by the medical imaging system using the determined configuration and calculating the position of the marker device from the marker image.

In one embodiment, the method involves calculating two or more configurations of the medical imaging system as described above, capturing a plurality of marker images, wherein a marker image is captured using each of the two or more configurations, and the position of the marker device is calculated from the plurality of marker images.

The present invention further relates, in a third aspect, to a computer program which, when running on a computer that is connected to or part of a medical imaging system comprising an x-ray source and an x-ray detector mounted on a gantry and an x-ray source collimator for shaping the beam of the x-ray source, wherein the at least one of the x-ray source and the x-ray detector is movable along the gantry, causes the computer to perform the steps of the method described above.

The present invention further relates, in a fourth aspect, to a computer on which the aforementioned computer program is stored and/or run.

The present invention still further relates, in a fifth aspect, to a non-transitory computer readable storage medium on which said program is stored.

Further, the present invention relates, in a sixth aspect, to a system comprising the aforementioned computer and a medical imaging system comprising an x-ray source and an x-ray detector mounted on a gantry and an x-ray source collimator for shaping the beam of the x-ray source. The medical imaging system has a configuration as described above.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of applying a medical instrument to the patient. More particularly, the invention does not involve or in particular comprise or encompass any surgical or therapeutic activity. The invention is instead directed as applicable to calculate a configuration which comprises parameters for operating a medical imaging system. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium which represents the program, for example the aforementioned program, which for example comprises code means which are adapted to perform any or all of the method steps described herein. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system or any other data processing machine.

Image Registration

Image registration is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

The position of a marker device can be ascertained. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Pointer

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Landmarks

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

Atlas/Atlas Segmentation

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

Elastic Fusion, Image Fusion/Morphing, Rigid Fusion

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

Fixed (Relative) Position

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another, for example by attaching a marker device to an object like a patient or to a medical instrument. The spatial location, which is a part of the position, can in particular be described just by a distance (between two objects) or just by the direction of a vector (which links two objects). The alignment, which is another part of the position, can in particular be described by just the relative angle of orientation (between the two objects).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
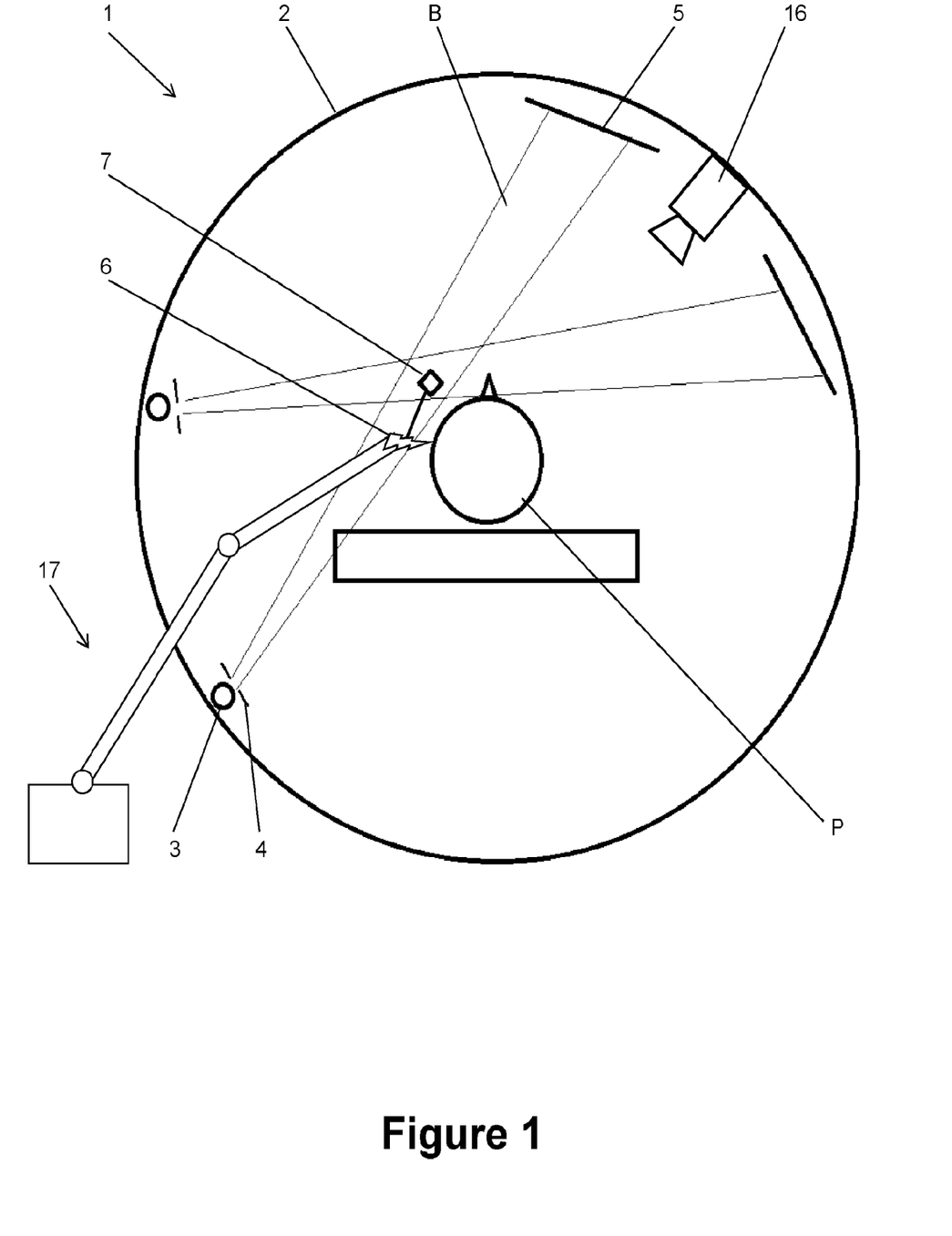
FIG. 1 shows a medical imaging system and a robot.

FIG. 1 shows a medical imaging system 1 and a robot 17. The medical imaging system 1 comprises a gantry 2 which carries an x-ray source 3, and x-ray source collimator 4 and an x-ray detector 5. In the present example, the gantry 2 is circular, like in the Loop-X® apparatus marketed by Brainlab AG.

The x-ray source 3 and the x-ray detector 5 are independently movable along the gantry 2 in a plane in which the gantry lies. The x-ray source collimator 4 is attached to the x-ray source 3 such that it moves along together with the x-ray source 3. The x-ray source 3 emits an x-ray beam which is typically conical and which is then collimated, or shaped, using the x-ray source collimator 4, resulting in a shaped x-ray beam B. During use, the shaped x-ray beam B passes through an object to be analyzed, such as the patient P, and detected using the x-ray detector 5. The x-ray detector 5 generates an x-ray image which can be analyzed by a processing unit (not shown in FIG. 1).

In the example shown in FIG. 1, the medical imaging system 1 comprises a single x-ray source 3, a single x-ray source collimator 4 and a single x-ray detector 5. However, those components are shown in two different positions in FIG. 1.

Also shown in FIG. 1 is a robot 17, in the present example comprising a base and an arm, wherein the arm comprises multiple segments and adjacent segments are connected via adjustable joints. At the free end of the arm, robot 17 carries a medical instrument 6. Attached to the medical instrument 6 is a marker device 7. Even though not shown in FIG. 1, the marker device 7 comprises multiple radiopaque markers in a known spatial arrangement. The position of the marker device 7 relative to the medical instrument 6 is known. The robot 17 is optional. The marker device 7 can be attached to any other object than the medical instrument 6 and/or the medical instrument 6 might not be attached to the free end of the robot 17, but for example be held by a human being.

The medical imaging system 1 has assigned an imaging system reference system, for example in terms of a co-ordinate system, which is used as a reference for all positions used by the present invention unless stated otherwise. The position of the base of the robot 17 in the image system reference system is for example known.

Figure 2:
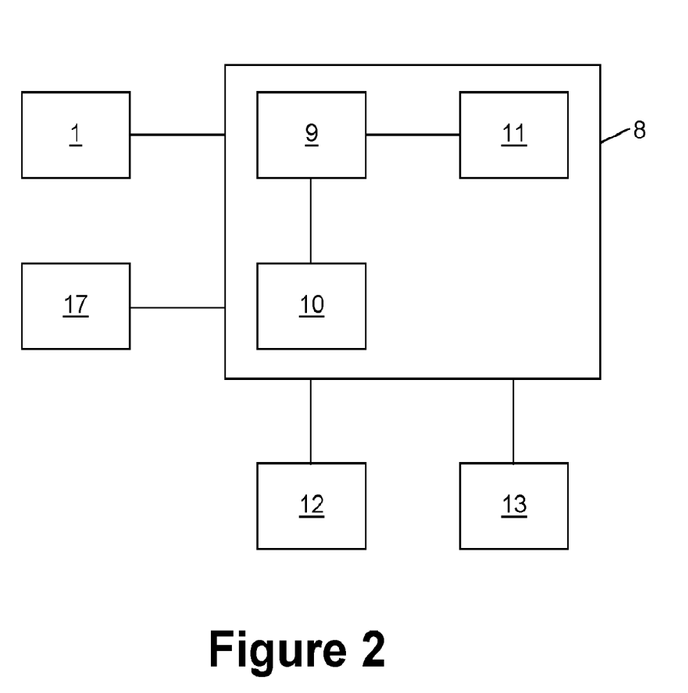
FIG. 2 shows a system comprising a computer, the medical imaging system and the robot.

FIG. 2 schematically shows a system according to the present invention. The system comprises a computer 8 having a central processing unit 9, an interface unit 10 and a memory 11. The memory 11 stores data, such as data to be processed or that have been processed, and instructions which let the central processing unit 9 perform the present invention. The interface connects the computer 8 to other components of the system, such as the medical imaging system 1 and the robot 17 if applicable. In this document, a connection between two components means that data can be transmitted from at least one component to the other component. The medical imaging system 1 can for example transmit a captured x-ray image to the computer 8. The computer 8 can transmit a configuration to the medical imaging system 1.

The robot 17 can transmit joint settings describing the settings of the joints between adjacent segments of the arm or of the joint between the arm and the base to the computer 8. The computer 8 can transmit control data to the robot 17, wherein the control data can describe the settings the joints of the robot shall assume.

The present invention utilizes the x-ray source 3, the x-ray source collimator 4 and the x-ray detector 5 for capturing a marker image showing at least a part of the marker device 7 such that the position of the marker device 7, and thus of the medical instrument 6, can be calculated in the reference system of the imaging system. Since the x-ray radiation used for generating an x-ray image might be harmful to the patient P, an aim of the present invention is finding a configuration of the medical imaging system such that a marker image can be captured with an acceptable radiation exposure on the patient P.

In the medical imaging system 1 as shown in FIG. 1, the configuration comprises the position of the x-ray source 3 on the gantry 2, the position of the x-ray detector 5 on the gantry 2 and the settings of the x-ray source collimator 4.

The computer 8 is further connected to an input device 12, such as a keyboard, a mouse, a trackball, a trackpad or a touchscreen, and to output device 13, such as a monitor.

Figure 3:
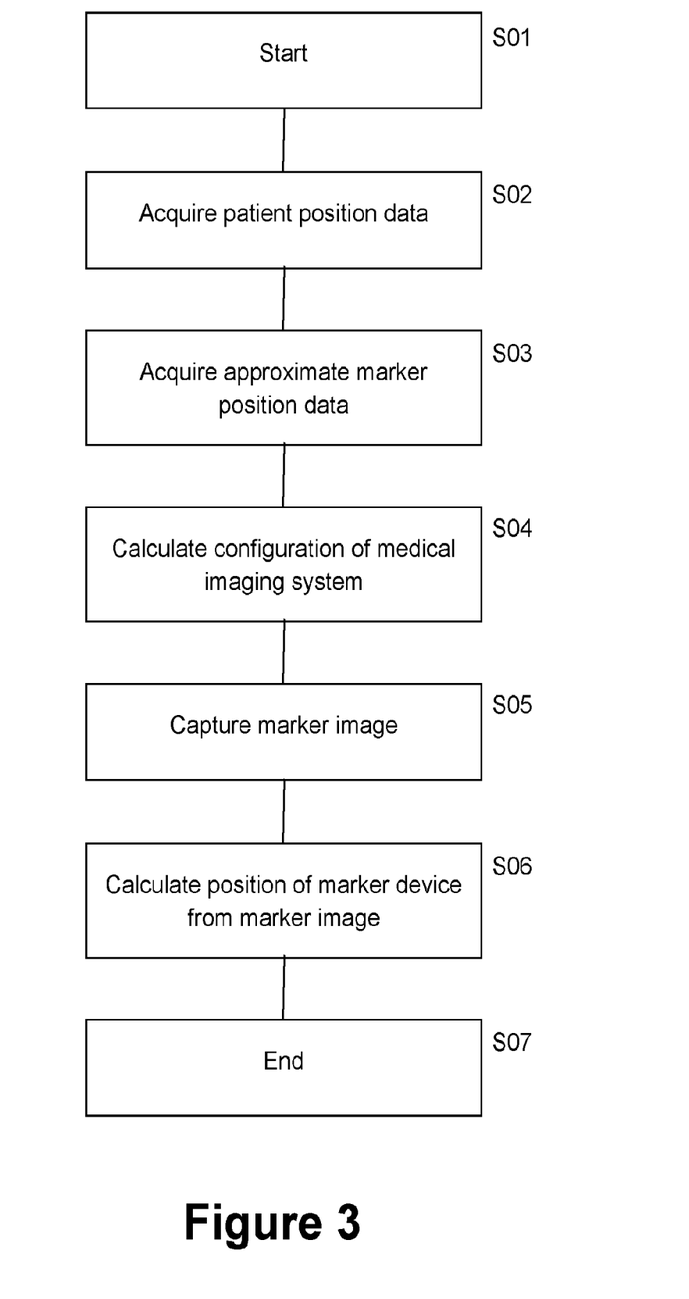
FIG. 3 shows a flow diagram of the method according to the present invention.

FIG. 3 shows a flow diagram of a method according to the present invention.

The process starts at step S01. At step S02, patient position data are acquired. The patient position data represent the position of the patient P relative to the medical imaging system 1, in particular in the imaging system reference system. The position of the patient P is for example given as the position of a patient reference system assigned to the patient P in the reference system of the medical imaging system 1.

There are multiple approaches for acquiring the patient position data. The simplest approach is acquiring a confirmation that the patient P is in a predetermined position relative to the medical imaging system 1, for example by entering a corresponding input via the input unit 12. Another approach involves capturing one or more x-ray image(s) using the medical imaging system 1 and performing 2D/3D registration of the captured x-ray image(s) with a three-dimensional image dataset of the patient P. Instead of using one or more x-ray image(s), one or more optical images, for example using an optical camera 16 of the medical imaging system 1, can be 2D/3D registered with a 3D image of the patient P. Yet another approach is sampling points on the surface of the patient P, in particular landmarks, for example using a pointer, and registering the sampled points with a 3D image of the patient P.

Step S03 involves acquiring approximate marker position data representing the approximate position of the marker device 7 relative to the medical imaging system 1. The approximate position of the marker device 7 is for example given in the reference system of the medical imaging system 1, in particular as the position of a marker reference system assigned to the marker device 7 in the reference system of the medical imaging system 1.

There are several approaches for determining the approximate marker position data. In one approach, the approximate marker position data can be calculated from the position of the base of the robot 17 in the reference system of the medical imaging system 1, a model of the robot 17, the positions of the joints of the robot 17, the position of the medical instrument 6 relative to the free end of the arm of the robot 17 and the position of the marker device 7 relative to the medical instrument 6. In another approach, the marker device 7 can be identified in an x-ray image of the patient P captured using the medical imaging system 1 and the approximate marker position can be calculated from the position of the marker device 7 in the x-ray image as well as the position of the x-ray source 3 and the position of the x-ray detector 5 when the x-ray image was captured.

Step S04 involves calculating the configuration of the medical imaging system 1 from the patient position data and the approximate marker position data and based on a trade-off between the radiation exposure on the patient P when capturing the marker image and a second criterion being at least one of the visibility of the marker device 7 in the marker image and the expected imaging quality of the marker device 7 in the marker image. Details of step S04 will be described later.

Step S05 involves capturing a marker image using the configuration calculated in step S04 and step S06 involves calculating the position of the marker device 7, in the reference system of the medical imaging system 1, from the marker image. The process ends at step S07.

It shall be noted that steps S05 and S06 are optional. The aim of the present invention is fulfilled once a suitable configuration of the medical imaging system 1 is found in step S04.

It might be advantageous to calculate the position of the marker device 7 from more than one marker image. In this case, step S04, and steps S05 and S06 if present, are repeated appropriately.

In one implementation of step S04, the trade-off is a metric which is optimized. The metric is calculated from sub-metrics, such as a radiation exposure metric representing the radiation exposure on the patient P, a visibility metric representing the visibility of the marker device 7 in the marker image and an imaging quality metric representing the expected imaging quality of the marker device 7 in the marker image.

Figure 4:
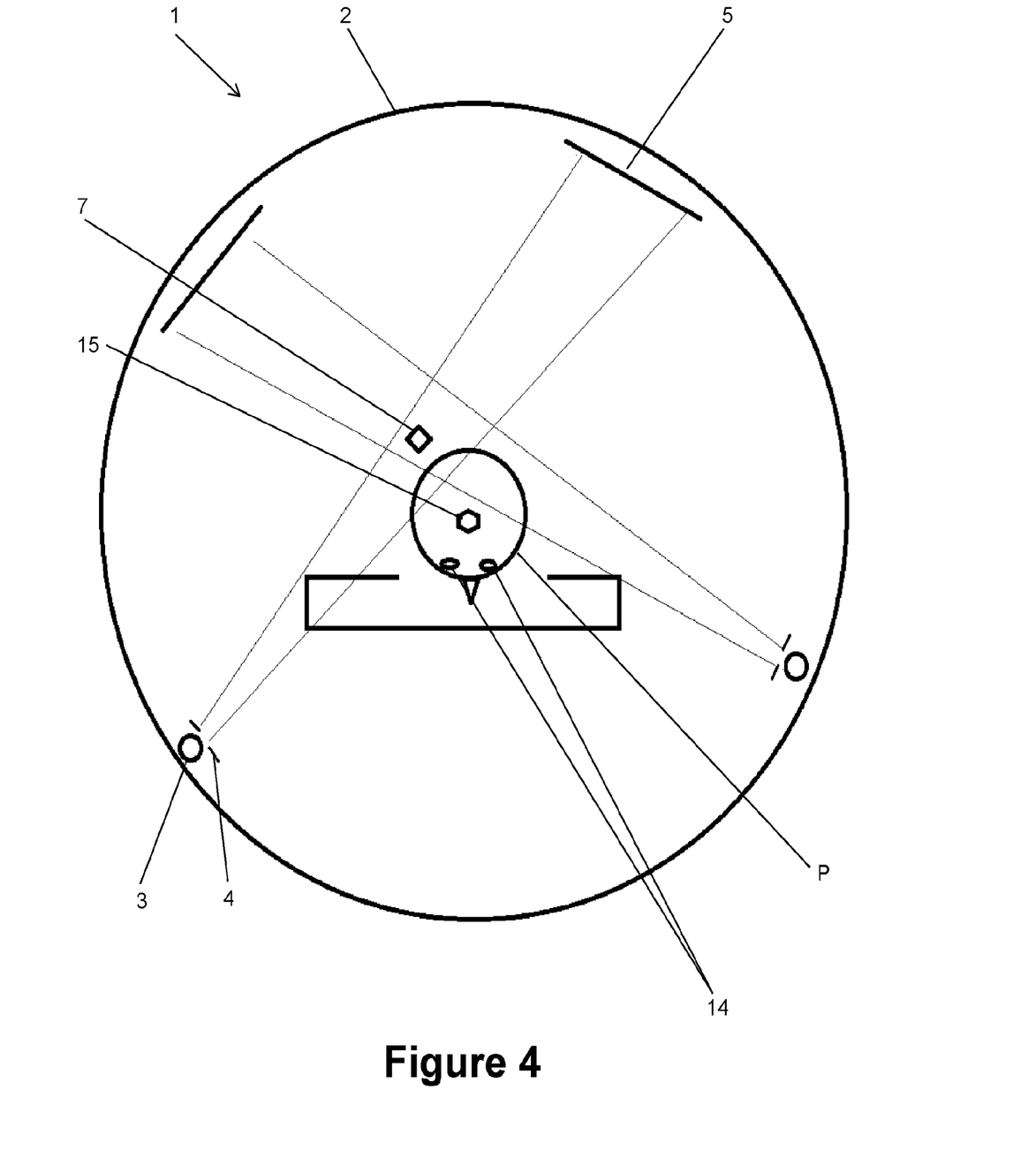
FIG. 4 shows an example for calculating the radiation exposure on the patient.

An approach for determining the radiation exposure metric is shown in FIG. 4. In this Figure, particular structures of the patient P, in this case eyes 14 and the brainstem 15, are shown. Those structures are particularly sensitive to x-ray radiation. For a particular configuration of the medical imaging system 1, the radiation exposure of the eyes 14, the brainstem 15 and the remaining tissue of the patient P can be calculated and combined to the radiation exposure metric by weighting the radiation exposure on the different structures appropriately. The position of the different structures in the reference system of the medical imaging system 1 can for example be determined by segmenting 3D image data of the patient P, for example using an atlas. The weights might also be taken from the atlas. In one example, the radiation exposure metric negatively correlates to the calculated radiation exposure on the patient P, for example linearly.

For a particular configuration of the medical imaging system 1, the visibility metric for example describes the portion of the marker device 7 which lies within the shaped x-ray beam B. In one example, the visibility metric positively correlates, for example linearly, to the portion of the marker device which lies within the shaped x-ray beam B. If, for example, the whole marker device 7 lies within the shaped x-ray beam B, the visibility metric is 1, and if only 70% of the marker device 7 lie within the shaped x-ray beam B, the visibility metric is 0.7.

The imaging quality metric can for example negatively correlate with the distance of the marker device 7 in the marker image from the center of the marker image. The distance can for example be calculated from the border of the marker device 7 which is closest to the center of the marker image or from the center of the marker device 7 in the marker image.

Figure 5:
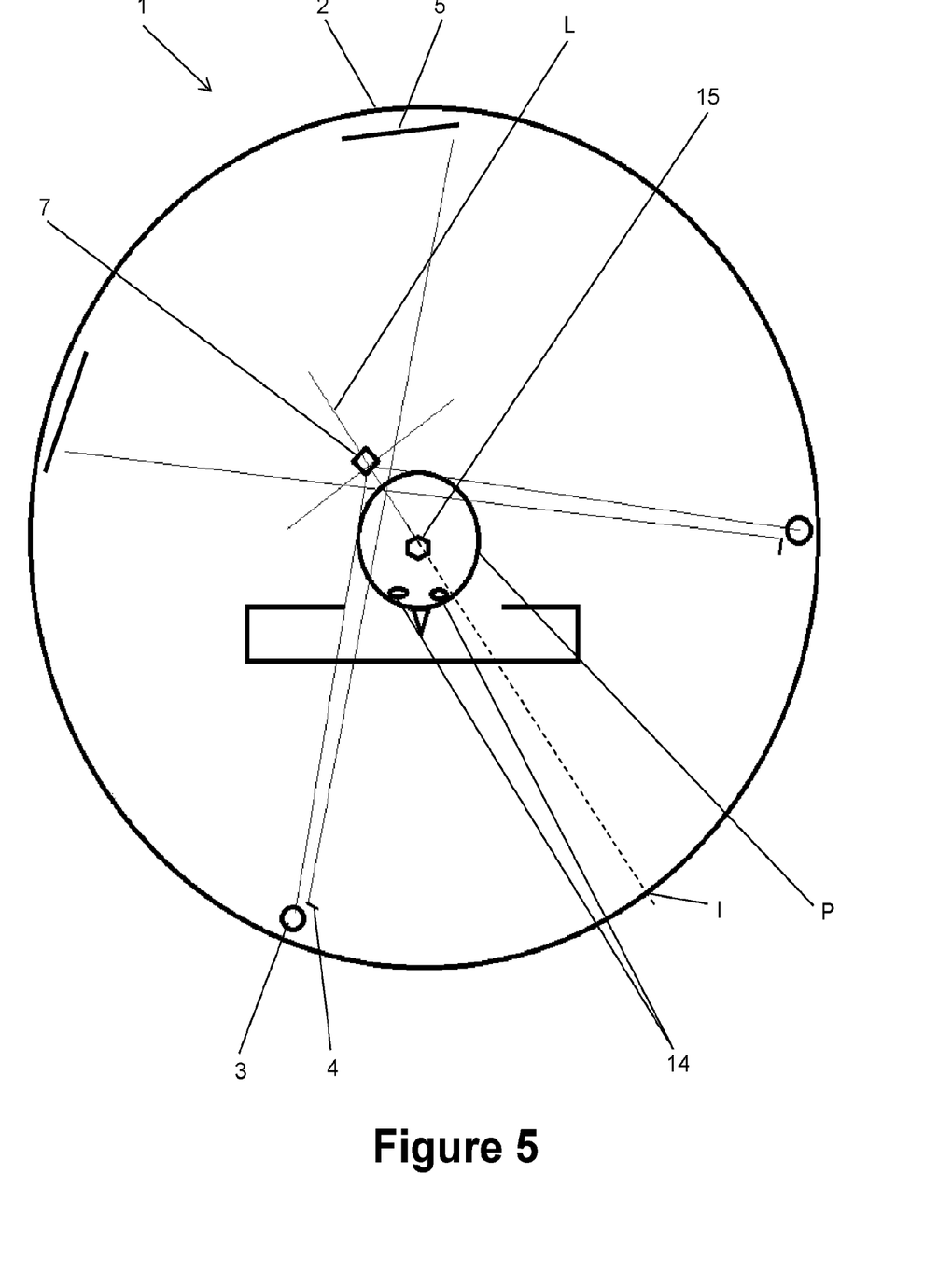
FIG. 5 shows an example for calculating a configuration of the medical imaging system.

FIG. 5 shows the scenario for another implementation of step S04 In this scenario, the approximate position of the marker device 7 and the center of a body part of the patient P, for example of the head of the patient P, are orthogonally projected into the plane in which the x-ray source 3 and the x-ray detector 5 can move along the circular gantry 2. Then a line L connecting the center of the body part and the marker device 7 is drawn in this plane and a point I at which this line L intersects with the gantry 2 is determined. For a first configuration of the medical imaging system 1, the position of the x-ray source 3 is set 45° clockwise from the point I and for a second configuration of the medical imaging system 1, the position of the x-ray source 3 is set at 45° anti-clockwise from the point I. The position of the x-ray detector 5 is, for example, always determined to be opposite to the position of the x-ray source 3 on the gantry 2.

With those positions of the x-ray source 3 and the x-ray detector 5 in each of the two configurations, corresponding settings of the x-ray source collimator 4 are calculated such that all of the marker device 7 lies within the corresponding shaped x-ray beam B. It is then determined whether or not the radiation exposure on the patient P when capturing the corresponding marker images would be acceptable. If it is, then the two configurations are selected. If it is not, the positions of the x-ray source 3 and the x-ray detector 5 are increased away from the point I, for example by 5°, the settings of the x-ray source collimator 4 are calculated again such that the marker device 7 fully lies within the shaped x-ray beam B, the corresponding radiation exposure on the patient P when capturing the marker images is calculated again and it is determined whether or not the radiation exposure is acceptable. If it is, the new configurations are selected. If it is not, the process is repeated.

The invention claimed is:

1. A method of determining a configuration setting for use by an associated medical imaging system including an x-ray source and an x-ray detector mounted on a gantry and an x-ray source collimator operable to shape an x-ray beam emitted by the x-ray source to determine a position of a marker device attached to an object, wherein at least one of the x-ray source and the x-ray detector is moveable along the gantry, the configuration setting of the medical imaging system comprising positions of the x-ray source and the x-ray detector and a parameter setting of the x-ray source collimator, the associated medical imaging system being operable to capture a marker image showing the marker device, the method comprising:
   acquiring patient position data representative of a position of a patient relative to the medical imaging system;
   acquiring approximate marker position data representative of an approximate position of the marker device relative to the medical imaging system; and
   calculating the configuration setting of the associated medical imaging system from the patient position data, the approximate marker position data and based on a trade-off between:
     a first criterion comprising minimizing a radiation exposure on the patient when capturing the marker image; and
     a second criterion comprising at least one of:
       maximizing a visibility of the marker device in the marker image; and/or
       maximizing an expected imaging quality of the marker device in the marker image,
   wherein the calculated configuration setting is usable by the associated medical imaging system to capture, based on the calculated configuration setting, a marker image that shows the marker device for determining the position of the marker device attached to the object.

2. The method of claim 1, wherein the calculating the configuration setting of the associated medical imaging system comprises:
   calculating a metric based on the radiation exposure and the second criterion; and
   optimizing the metric.

3. The method of claim 1, wherein the trade-off comprises a size of the shaped x-ray beam.

4. The method of claim 1, wherein, if a plurality of two or more marker images is to be captured, the trade-off represents viewing directions between the shaped x-ray beams emitted when the plurality of two or more marker images are captured.

5. The method of claim 1, wherein the acquiring the approximate marker position data comprises acquiring the approximate marker position data based on at least one of an x-ray image of the patient that also shows at least part of the marker device, position data obtained from an associated medical tracking system, planning data describing a procedure to be performed using the medical imaging system, optical image data obtained by an optical camera of the associated medical imaging system, and robot position data representing a position of an associated robot carrying the marker device.

6. The method of claim 1, wherein the acquiring the patient position data comprises acquiring the patient position data based on at least one of a 3D scan of the patient, sampling a plurality of points on a surface of the patient, and performing 2D/3D registration of 3D image data of the patient with one or multiple two-dimensional images of the patient.

7. The method of claim 1, wherein the visibility of the marker device represents at least one of a portion of the marker device that lies within the shaped x-ray beam and an orientation of the marker device relative to the x-ray source.

8. The method of claim 1, further comprising calculating the radiation exposure on the patient as an overall x-ray dose applied to the patient or as the sum of the x-ray dose applied to different regions of the patient multiplied by weight factors corresponding to said different regions.

9. The method of claim 1, wherein the calculating the configuration setting of the associated medical imaging system comprises:
    calculating a preliminary configuration setting of the associated medical imaging system, capturing a preliminary marker image by the associated medical imaging system using the preliminary configuration setting, and calculating the approximate marker position data from the preliminary marker image; and
    calculating the configuration setting of the associated medical imaging system based on the approximate marker position data.

10. The method of claim 1, wherein, if the associated medical imaging system is to be used for determining the position of multiple marker devices, the method further comprises calculating the configuration setting of the associated medical imaging system from the patient position data, the approximate marker position data of all marker devices, and based on a trade-off between:
    the radiation exposure on the patient when capturing the marker image, and
    the second criterion being at least one of:
        the visibility of at least one of the marker devices in the marker image, and
        the expected imaging quality of at least one of the marker devices in the marker image.

11. A method of determining a position of a marker device relative to an associated medical imaging system comprising an x-ray source and an x-ray detector mounted on a gantry and an x-ray source collimator for shaping a beam of the x-ray source to determine a position of the marker device attached to an object, wherein at least one of the x-ray source and the x-ray detector is moveable along the gantry, the method comprising:
    determining a configuration setting for use by the medical imaging system by:
        acquiring patient position data representative of a position of a patient relative to the medical imaging system;
        acquiring approximate marker position data representative of an approximate position of the marker device relative to the medical imaging system; and
        calculating the configuration setting of the associated medical imaging system from the patient position data, the approximate marker position data and based on a trade-off between:
            a first criterion comprising minimizing a radiation exposure on the patient when capturing a marker image of the marker device attached to the object; and
            a second criterion comprising at least one of:
                maximizing a visibility of the marker device in the marker image; and/or
                maximizing an expected imaging quality of the marker device in the marker image, wherein the calculated configuration setting is usable by the associated medical imaging system to capture, based on the calculated configuration setting, a marker image that shows the marker device for determining the position of the marker device attached to the object;
    capturing a marker image by the medical imaging system, using the determined configuration setting; and
    calculating the position of the marker device from the marker image.

12. A non-transient computer readable storage medium storing a computer program that, when executed by a processor of a computer that is connected to or part of an associated medical imaging system comprising an x-ray source and an x-ray detector mounted on a gantry and an x-ray source collimator for shaping a beam of the x-ray source to determine a position of a marker device attached to an object, wherein at least one of the x-ray source and the x-ray detector is moveable along the gantry, causes the computer to perform a method comprising:
    acquiring patient position data representative of a position of the patient relative to the medical imaging system;
    acquiring approximate marker position data representative of an approximate position of the marker device relative to the medical imaging system; and
    calculating a configuration setting of the associated medical imaging system from the patient position data, the approximate marker position data and based on a trade-off between:
        a first criterion comprising minimizing a radiation exposure on the patient when capturing a marker image of the marker device attached to the object; and
        a second criterion comprising at least one of:
            maximizing a visibility of the marker device in the marker image; and/or
            maximizing an expected imaging quality of the marker device in the marker image,
    wherein the calculated configuration setting is usable by the associated medical imaging system to capture, based on the calculated configuration setting, a marker image that shows the marker device for determining the position of the marker device attached to the object.

13. A system comprising:
a medical imaging system comprising an x-ray source and an x-ray detector mounted on a gantry and an x-ray source collimator for shaping a beam of the x-ray source to determine a position of a marker device attached to an object; and
a computer comprising a processor and non-transient computer readable storage medium storing a computer program that, when executed by the processor performs a method comprising:
    acquiring patient position data representative of a position of a patient relative to the medical imaging system;
    acquiring approximate marker position data representative of an approximate position of a marker device relative to the medical imaging system; and
    calculating a target configuration setting of the medical imaging system from the acquired patient position data, the acquired approximate marker position data, and based on a trade-off between:

a first criterion comprising minimizing a radiation exposure on the patient when capturing a marker image of the marker device attached to the object; and a second criterion comprising at least one of:
maximizing a visibility of the marker device in the marker image; and/or
maximizing an expected imaging quality of the marker device in the marker image, wherein the calculated target configuration setting is usable by the medical imaging system to capture, based on the calculated target configuration setting, a marker image that shows the marker device for determining the position of the marker device attached to the object.

* * * * *